United States Patent
Dalko et al.

(10) Patent No.: US 9,833,397 B2
(45) Date of Patent: Dec. 5, 2017

(54) ANTI-DANDRUFF SUGARS

(71) Applicant: L'OREAL, Paris (FR)

(72) Inventors: Maria Dalko, Versailles (FR); Julien Hitce, Paris (FR); Laure Ramos-Stanbury, Sceaux (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/429,793

(22) PCT Filed: Sep. 19, 2013

(86) PCT No.: PCT/EP2013/069527
§ 371 (c)(1),
(2) Date: Mar. 20, 2015

(87) PCT Pub. No.: WO2014/044779
PCT Pub. Date: Mar. 27, 2014

(65) Prior Publication Data
US 2015/0250698 A1 Sep. 10, 2015

Related U.S. Application Data

(60) Provisional application No. 61/724,560, filed on Nov. 9, 2012.

(30) Foreign Application Priority Data

Sep. 21, 2012 (FR) ...................................... 12 58905

(51) Int. Cl.
*A61K 8/60* (2006.01)
*A61Q 5/00* (2006.01)
*C07H 15/04* (2006.01)
*C07H 15/10* (2006.01)
*A61Q 5/02* (2006.01)

(52) U.S. Cl.
CPC .............. *A61K 8/602* (2013.01); *A61Q 5/006* (2013.01); *A61Q 5/02* (2013.01); *C07H 15/04* (2013.01); *C07H 15/10* (2013.01)

(58) Field of Classification Search
None
See application file for complete search history.

(56) References Cited

FOREIGN PATENT DOCUMENTS

| | | |
|---|---|---|
| DE | 19547160 A1 | 6/1997 |
| FR | 2712890 A1 | 6/1995 |
| FR | 2929509 A1 | 10/2009 |
| JP | H08508033 A | 8/1996 |
| JP | 2003534446 A | 11/2003 |
| JP | 2011026282 A | 2/2011 |
| WO | WO-9421655 A1 | 9/1994 |
| WO | WO-97/45101 A1 | 12/1997 |
| WO | WO-01/90286 A1 | 11/2001 |
| WO | WO-02/47652 A1 | 6/2002 |

OTHER PUBLICATIONS

Sato, Chemistry Letters vol. 33, No. 5 (2004).*
Petit, FR 2712890 A1, Jun. 2, 1995, machine translation.*
Matsumura et al., "Surface Activities, Biodegradability and Antimicrobial Properties of n-Alkyl Glucosides, Mannosides and Galactosides", Journal of the American Oil Chemists' Society, vol. 67, No. 12, Dec. 1, 1990, pp. 996-1001.

* cited by examiner

*Primary Examiner* — Layla Berry
(74) *Attorney, Agent, or Firm* — Polsinelli PC

(57) ABSTRACT

The invention relates to the cosmetic use of at least one compounds according to the following formula (I), as an anti-dandruff agent or for preventing and/or treating scalp dandruff: where "sugar" denotes a monosaccharide residue chosen from rhamnose, xylose, fucose, mannose, lyxose, and arabinose; where R, substituting the anomeric oxygen in the sugar (represented by "O" in formula (I)), denotes a radical comprising 6 to 38 carbon atoms chosen from: —a linear or branched, saturated alkyl radical; —a linear or branched, alkenyl radical; said linear or branched saturated alkyl radical being optionally substituted by at least one OH and/or NH2 function; —if "sugar" denotes a mannose residue, R denotes a linear C6-C38 alkyl radical, substituted by at least one OH function or an NH2 function; and the salts and solvates and/or optical isomers thereof, alone or in a mixture, particularly racemic forms. The invention also relates to compounds according to formula (I), and cosmetic compositions containing same.

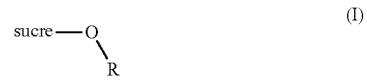

(I)

20 Claims, No Drawings

ANTI-DANDRUFF SUGARS

CROSS REFERENCE TO RELATED APPLICATIONS

This application is a National Phase filing under 35 U.S.C. §371 of PCT/EP2013/069527 filed on Sep. 19, 2013; and this application claims priority to Application No. 1258905 filed in France on Sep. 21, 2012, and claims the benefit of U.S. Provisional Application No. 61/724,560 filed on Nov. 9, 2012, under 35 U.S.C. §119. The entire contents of each application are hereby incorporated by reference.

The present invention relates to the use of specific sugars as anti-dandruff agents. The invention also relates to a cosmetic treatment method for eliminating and/or reducing dandruff. The invention also relates to specific compounds, and compositions comprising same.

The appearance of dandruff, due to a scalp desquamation disorder, is troublesome both in terms of personal appearance and the discomfort caused (itching, rash, etc.), so much so that many people suffering from this problem to variable degrees seek an effective and definitive removal method.

Dandruff is caused by visible excessive scalp desquamation, resulting from excessively rapid epidermal cell multiplication. This phenomenon may be caused particularly by physical or chemical microtraumas, such as overly aggressive hair treatments, extreme weather conditions, nerves, diet, fatigue, pollution; however, it has been demonstrated that dandruff is most often the result of a scalp microflora disorder, and more particularly excessive colonization of a yeast belonging the *Malassezia* genus family of yeasts (previously known as *Pytirosporum ovale*) which is naturally found on the scalp.

To control dandruff, the use of topical anti-fungal agents is known. Using the anti-fungal potential thereof, these agents are intended to eliminate or control the multiplication of a resident yeast on the scalp, belonging to the *Malassezia* genus and the variants thereof (*M. ovalis, M. orbiculare, M. furfur, M. globose*, etc.).

Numerous agents are claimed, known and used for this purpose, including Zinc Pyrithione, Piroctone Olamine, Selenium Disulfide.

However, these anti-dandruff agents are not fully satisfactory in terms of efficacy (immediate efficacy or duration of effect).

The aim of the present invention is that of providing anti-dandruff agents which are as effective as known anti-dandruff agents, while having satisfactory cosmetic properties.

Another aim of the invention is to provide active agents which make it possible to re-establish the ecoflora of the scalp and in particular to prevent colonization of the scalp by *Malassezia* sp. in order to remove or reduce the amount of dandruff.

The present invention relates to active compounds (hereinafter referred to as "agents") in the field of scalp care and the use thereof particularly as anti-dandruff agents.

The applicant has now surprisingly discovered that the use of some compounds according to formula (I) as defined hereinafter helps treat dandruff effectively, and remedy the drawbacks of the prior art.

The compounds according to formula (I) also provide satisfactory cosmetic properties, in particular, the treated hair has a soft, non-sticky, non-greasy texture, is easy to comb, is free from unpleasant odors and good resistance, rendering the application thereof pleasant on the scalp.

In this way, using the compounds according to the invention, dandruff may be eliminated and/or the number of dandruff flakes reduced. In other words, the invention relates to the topical cosmetic use of specific sugar derivatives for preventing and/or treating scalp dandruff.

The present invention thus relates to the cosmetic use of at least one compound according to formula (I) as an active, particularly as an anti-dandruff agent or for preventing and/or treating scalp dandruff. The expression "preventing and/or treating dandruff" particularly refers to preventing excessive dandruff formation, and/or visually unappealing excessively formed dandruff.

The invention also relates to a cosmetic treatment method for preventing and/or treating dandruff, characterized in that it comprises the application, on the scalp, of at least one compound according to formula (I), or of a cosmetic composition containing said at least one compound.

The compounds according to the invention are represented by the following formula (I):

(I)

where "sugar" denotes a monosaccharide residue chosen from rhamnose, xylose, fucose, mannose, lyxose, and arabinose;

where R, substituting the anomeric oxygen in the sugar (represented by "O" in formula (I)), denotes a radical comprising 6 to 38 carbon atoms chosen from:
 a linear or branched, saturated alkyl radical;
 a linear or branched, alkenyl radical;
 said linear or branched saturated alkyl radical being optionally substituted by at least one OH and/or NH2 function;
 if "sugar" denotes a mannose residue, R denotes a linear C6-C38 alkyl radical, substituted by at least one OH function or an NH2 function.

The invention also covers salts, solvates and/or optical isomers, alone or in a mixture, particularly the racemic forms of the compounds according to the invention.

According to one alternative embodiment of the invention, the sugar is a pyranose.

According to one alternative embodiment, the sugar is a pyranose not comprising a pendant (lateral) —CH2OH group.

Preferably, the sugar is: L-rhamnose, D-xylose, L-fucose, D-mannose, D-lyxose, or arabinose.

According to one alternative embodiment, the sugar is chosen from:
 6-deoxy-L-mannopyranoside;
 6-deoxy-L-galactopyranoside;
 D-xylopyranoside;
 D-lyxopyranoside; and
 L-arabinopyranoside.

More particularly, the compounds according to formula (I) comprise a radical R comprising 8 to 30 carbon atoms.

According to a first advantageous alternative embodiment, the compounds according to the invention are represented by the following formula (II):

(II)

and the salts and solvates, and/or optical isomers thereof, alone or in a mixture, particularly the racemic forms,
 where "sugar" has the meaning above;
 where R1, substituting anomeric oxygen, denotes:
 a linear or branched, saturated C8-C22 alkyl radical;
 a linear or branched, C8-C22 alkenyl radical;
 a linear C8-C22 alkyl radical, substituted by an OH function or an NH2 function;

if "sugar" denotes a D-mannose residue, R1 denotes a linear C8-C22 alkyl radical, substituted by an OH or NH2 function.

Preferably, R1 denotes a C8-C20 saturated linear alkyl radical. Preferentially, R1 denotes a C12-C20 saturated linear alkyl radical. More preferentially, R1 denotes a C14-C18 saturated linear alkyl radical.

As compounds according to formula (II), at least one of the compounds hereinafter or any of the mixtures thereof may be used:

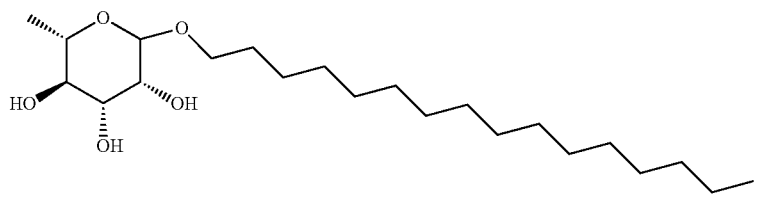

hexadecyl 6-deoxy-L-mannopyranoside (rhamnose sugar)

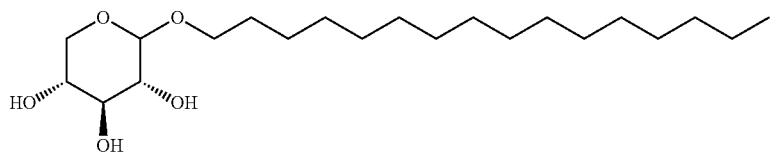

hexadecyl D-xylopyranoside (xylose sugar)

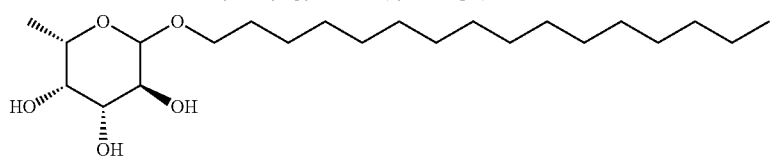

hexadecyl 6-deoxy-L-galactopyranoside (fucose sugar)

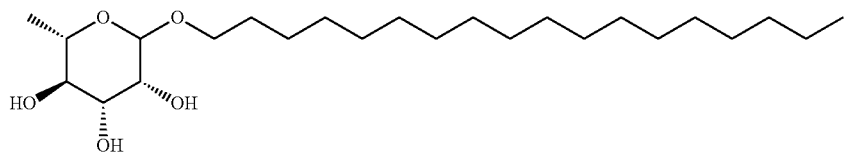

octadecyl 6-deoxy-L-mannopyranoside (rhamnose sugar)

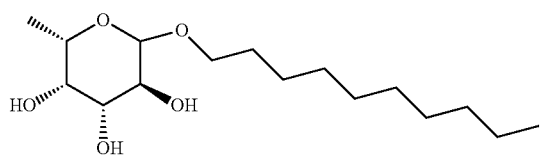

decyl 6-deoxy-L-galactopyranoside (fucose sugar)

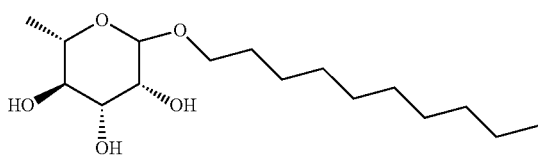

decyl 6-deoxy-L-mannopyranoside (rhamnose sugar)

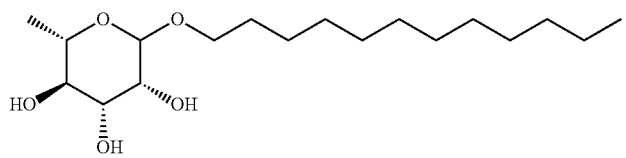

dodecyl 6-deoxy-L-mannopyranoside (rhamnose sugar)

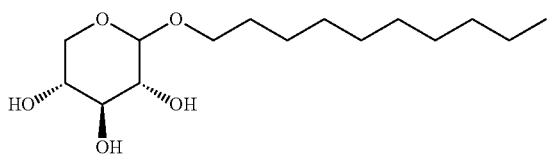

decyl D-xylopyranoside (xylose sugar)

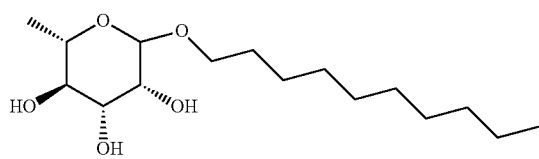

docosyl 6-deoxy-L-mannopyranoside (rhamnose sugar)

-continued

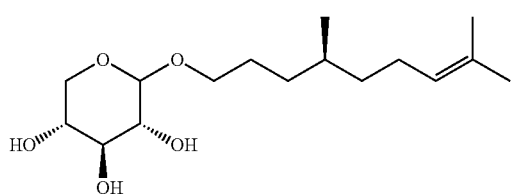

(3S)-3,7-dimethyloct-6-en-1-yl D-xylopyranoside (xylose sugar)

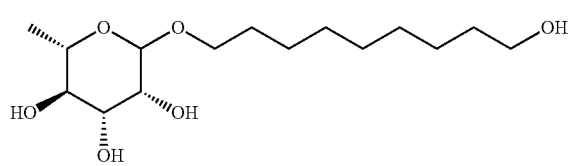

9-hydroxynonyl 6-deoxy-L-mannopyranoside (rhamnose sugar)

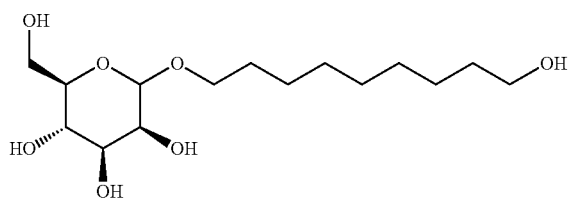

9-hydroxynonyl -D-mannopyranoside (mannose sugar)

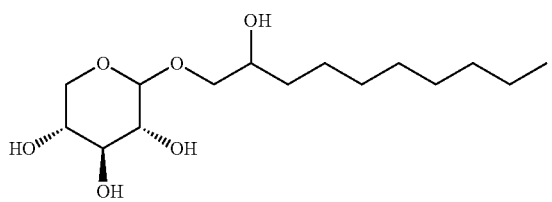

2-hydroxydecyl D-xylopyranoside (xylose sugar)

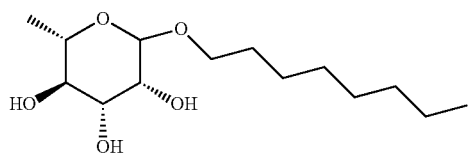

octyl 6-deoxy-L-mannopyranoside (rhamnose sugar)

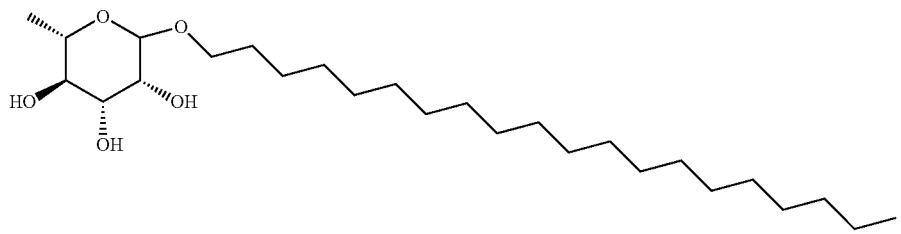

eicosyl 6-deoxy-L-mannopyranoside (rhamnose sugar)

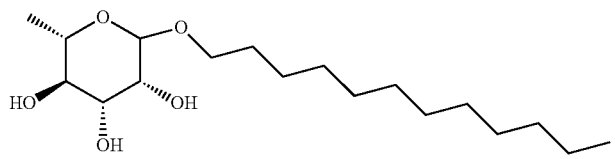

dodecyl 6-deoxy-L-mannopyranoside (rhamnose sugar)

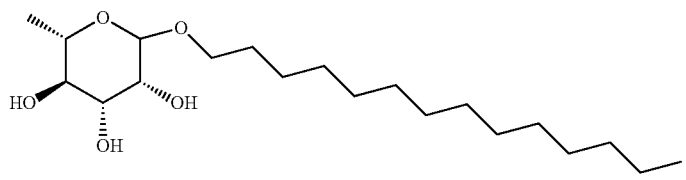

tetradecyl 6-deoxy-L-mannopyranoside (rhamnose sugar)

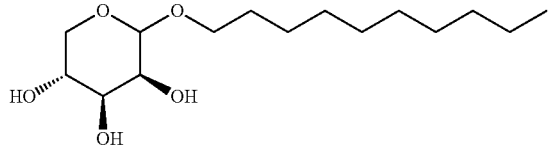

decyl D-lyxopyranoside (lyxose sugar)

According to a second advantageous alternative embodiment, particularly preferred compounds are represented by the following formula (III):

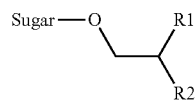
(III)

and the salts and solvates and/or optical isomers thereof, alone or in a mixture, particularly racemic forms, where "sugar" denotes a monosaccharide residue chosen from rhamnose, xylose, fucose, mannose, lyxose, and arabinose;

R1 denotes a linear C2-C18 alkyl radical;

R2 denotes a linear C2-C18 alkyl radical.

Preferably, R1 denotes a C2, C4, C6, C8, C10, C12, C14, C16, or C18 linear alkyl radical.

Preferably, R2 denotes a C2, C4, C6, C8, C10, C12, C14, C16, or C18 linear alkyl radical.

Preferentially, R1 denotes a C6-C10 linear alkyl radical and R2 denotes a C8-C12 linear alkyl radical.

As compounds according to formula (III), the following may be used alone or in any of the mixtures thereof:

TABLE 1

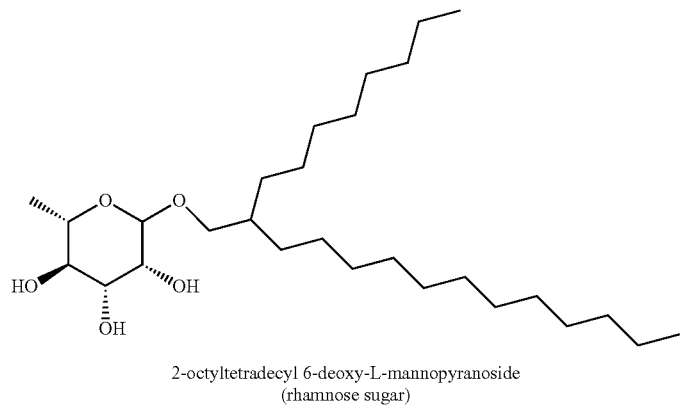 [SMILES: CCCCCCCCCCCCC(CCCCCCCC)COC1O[C@@H](C)[C@H](O)[C@@H](O)[C@H]1O]

2-octyltetradecyl 6-deoxy-L-mannopyranoside
(rhamnose sugar)

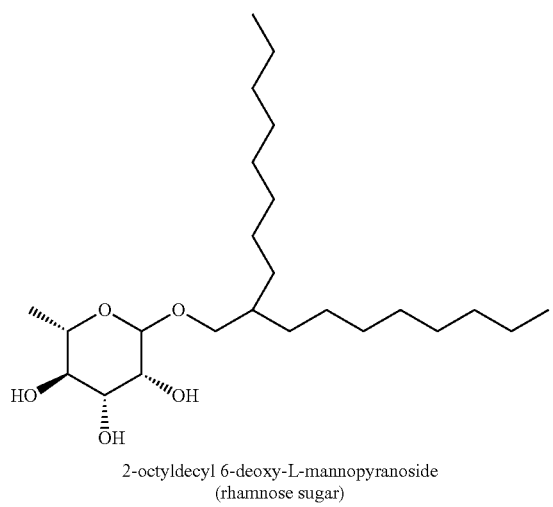 [SMILES: CCCCCCCCC(CCCCCCCC)COC1O[C@@H](C)[C@H](O)[C@@H](O)[C@H]1O]

2-octyldecyl 6-deoxy-L-mannopyranoside
(rhamnose sugar)

TABLE 1-continued
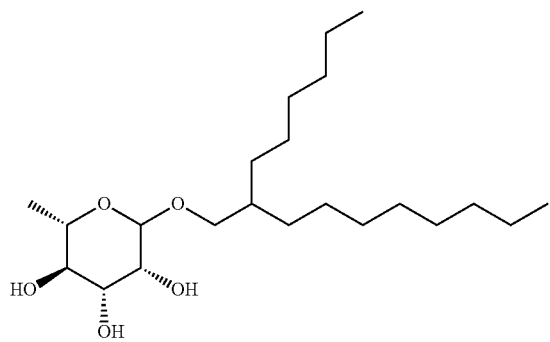
example B-1
2-hexyldecyl 6-deoxy-L-mannopyranoside
(rhamnose sugar)
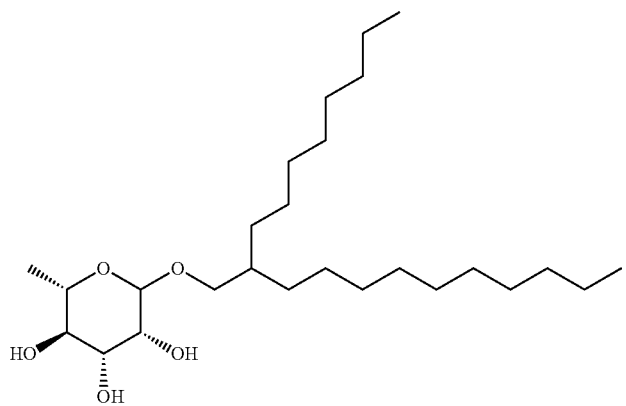
example B-2
2-octyldodecyl 6-deoxy-L-mannopyranoside
(rhamnose sugar)
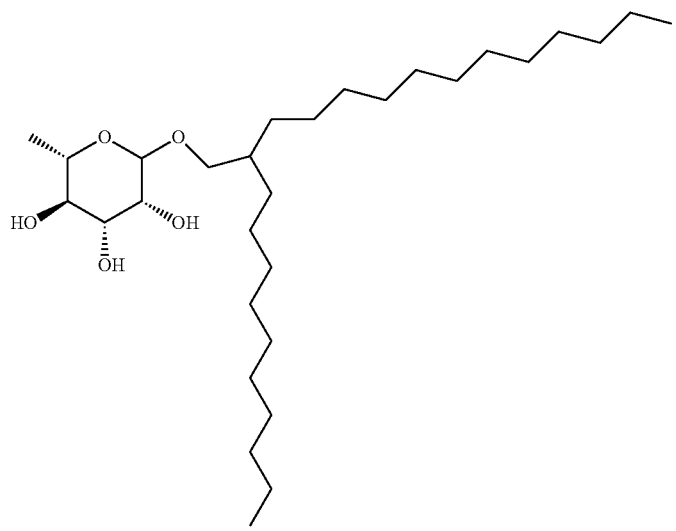
example B-3
2-decyltetradecyl 6-deoxy-L-mannopyranoside
(rhamnose sugar)

TABLE 1-continued
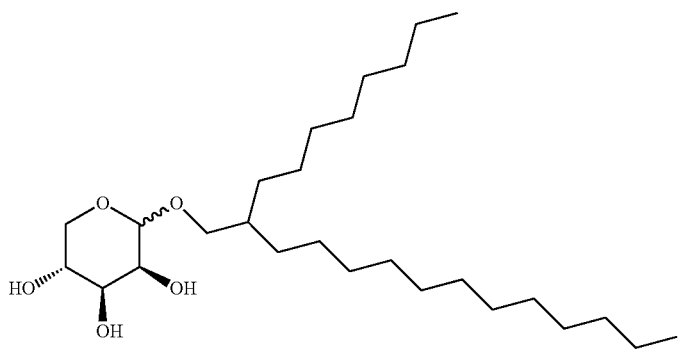
2-octyltetradecyl D-lyxopyranoside
(lyxose sugar)
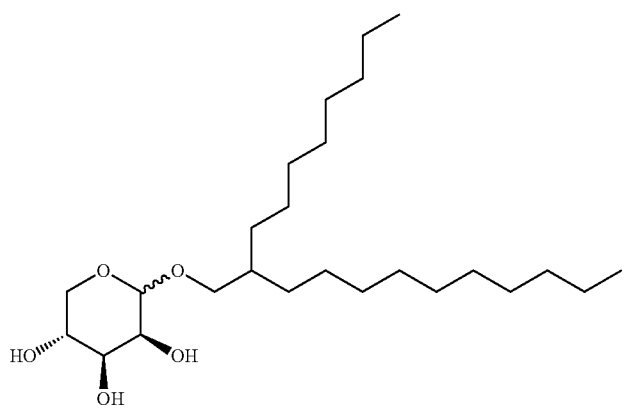
2-octyldodecyl D-lyxopyranoside
(lyxose sugar)
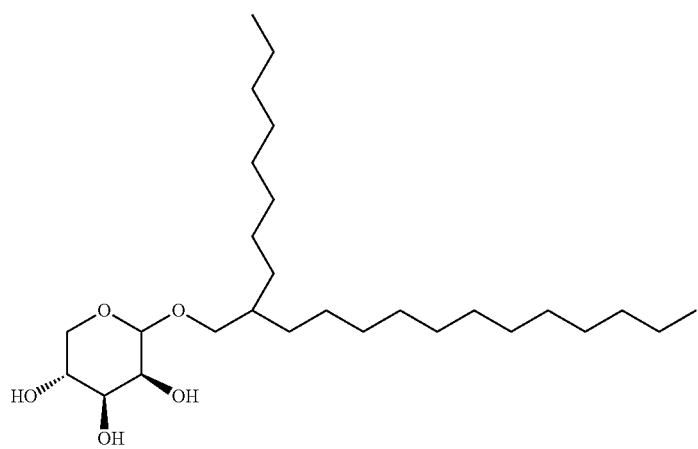
2-decyltetradecyl D-lyxopyranoside
(lyxose sugar)

TABLE 1-continued
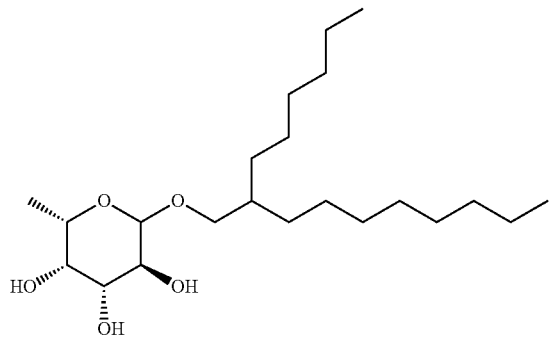
2-hexyldecyl 6-deoxy-L-galactopyranoside
(fucose sugar)
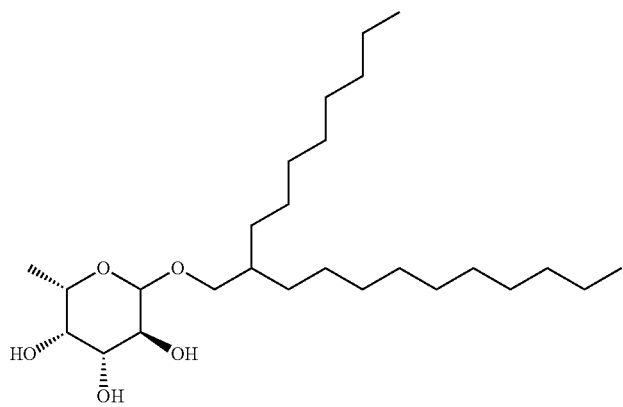
2-octyldodecyl 6-deoxy-L-galactopyranoside
(fucose sugar)
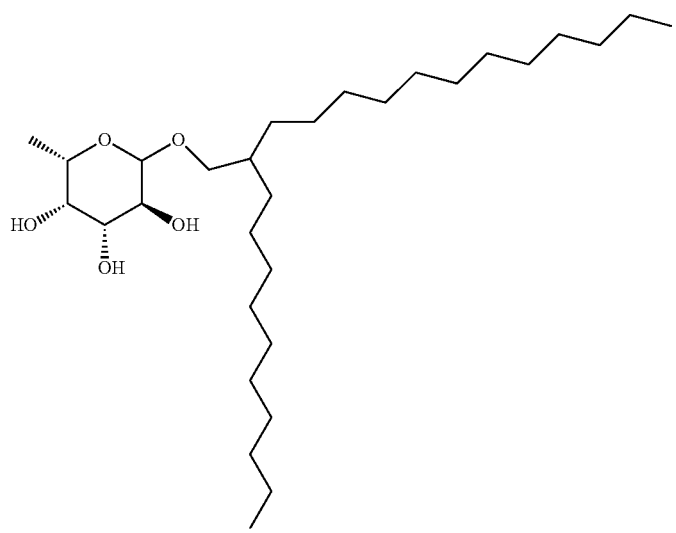
2-decyltetradecyl 6-deoxy-L-galactopyranoside
(fucose sugar)

TABLE 1-continued
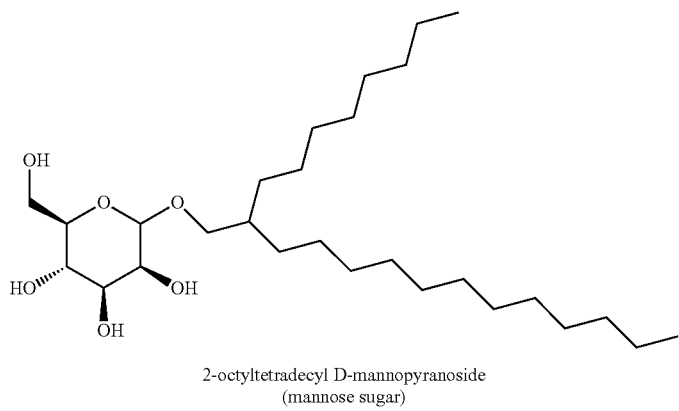 [SMILES: CCCCCCCCCCCCC(CCCCCCCC)COC1O[C@H](CO)[C@@H](O)[C@H](O)[C@@H]1O]
2-octyltetradecyl D-mannopyranoside
(mannose sugar)
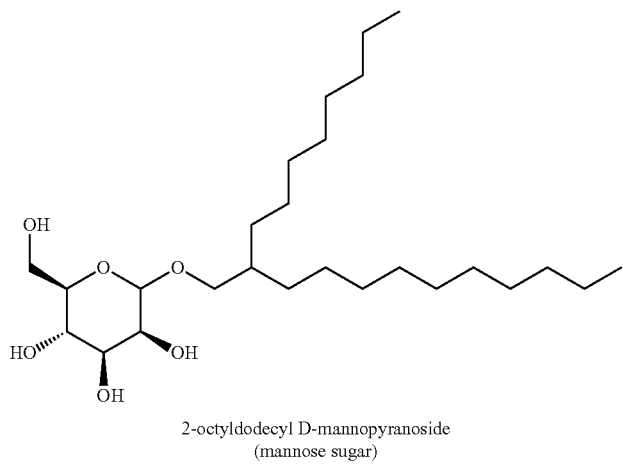 [SMILES: CCCCCCCCCCC(CCCCCCCC)COC1O[C@H](CO)[C@@H](O)[C@H](O)[C@@H]1O]
2-octyldodecyl D-mannopyranoside
(mannose sugar)
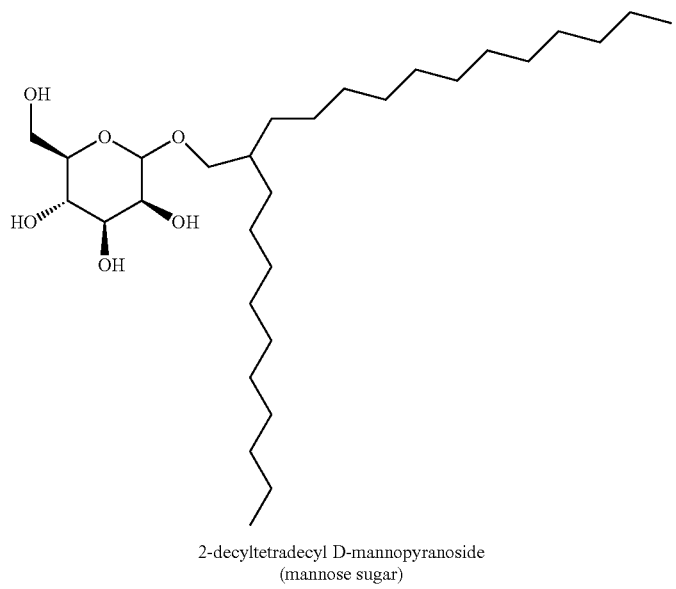 [SMILES: CCCCCCCCCCCCC(CCCCCCCCCC)COC1O[C@H](CO)[C@@H](O)[C@H](O)[C@@H]1O]
2-decyltetradecyl D-mannopyranoside
(mannose sugar)

TABLE 1-continued

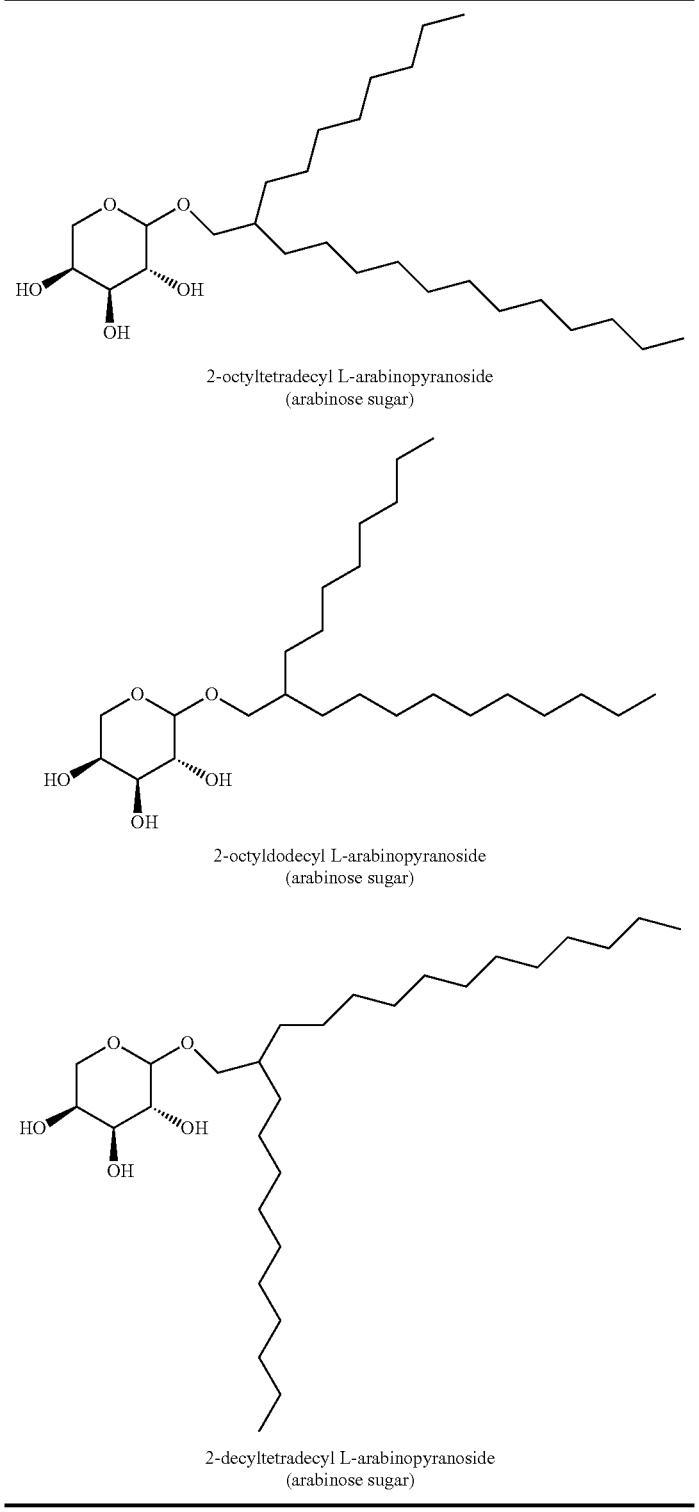

2-octyltetradecyl L-arabinopyranoside
(arabinose sugar)

2-octyldodecyl L-arabinopyranoside
(arabinose sugar)

2-decyltetradecyl L-arabinopyranoside
(arabinose sugar)

The invention also relates to novel compounds according to formula (I')

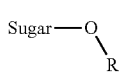

(I')

and the salts and solvents and/or optical isomers thereof, alone or in a mixture, particularly the racemic forms wherein, the sugar is a rhamnose and R is a C6-C38 linear alkyl radical substituted by an OH function;

the sugar is a rhamnose and R is a C8-C38 linear alkyl radical substituted by an NH2 function;

the sugar is a mannose and R is a C8-C38 linear alkyl radical substituted by an OH function;
the sugar is a mannose and R is a C11-C38 linear alkyl radical substituted by an NH2 function;
the sugar is a xylose and R is a C6-C38 linear alkyl radical substituted by an OH function;
the sugar is a xylose and R is a C9-C38 linear alkyl radical substituted by an NH2 function;
the sugar is a lyxose and R is a C6-C38 linear alkyl radical substituted by an OH function;
the sugar is a lyxose and R is a C6-C38 linear alkyl radical substituted by an NH2 function;
the sugar is a fucose and R is a C6-C38 linear alkyl radical substituted by an OH function;
the sugar is a fucose and R is a C9-C38 linear alkyl radical substituted by an NH2 function;
the sugar is an arabinose and R is a C6-C38 linear alkyl radical substituted by an OH function;
the sugar is an arabinose and R is a C9-C38 linear alkyl radical substituted by an NH2 function,
or
the sugar denotes a monosaccharide residue chosen from rhamnose, fucose, lyxose, and arabinose, and R represents:

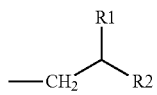

where
R1 denotes a linear C2-C18 alkyl radical; and
R2 denotes a linear C2-C18 alkyl radical.

Examples of compounds according to formula (I') include:
9-hydroxynonyl 6-deoxy-L-mannopyranoside
9-hydroxynonyl-D-mannopyranoside
2-hydroxydecyl D-xylopyranoside
and the specific compounds according to formula (III) cited above.

One or a plurality of compounds according to the invention, in any of the combinations thereof, are advantageously present in a cosmetic composition containing a physiologically acceptable medium.

In this way, the invention covers a cosmetic composition comprising at least one compound as defined according to the invention and a physiologically acceptable medium.

The term physiologically acceptable medium refers to a medium compatible with cutaneous tissue such as the skin and scalp.

One or a plurality of compounds according to the invention may be present in the cosmetic composition at a content ranging from 0.01 to 20% by weight, relative to the total weight of the cosmetic composition, preferably ranging from 0.05 to 15% by weight, preferentially ranging from 0.1 to 10% by weight, and more preferentially ranging from 0.1 to 5% by weight.

The physiologically acceptable medium of the composition may more particularly consist of water and optionally a physiologically acceptable organic solvent chosen for example from lower alcohols comprising 2 to 8 carbon atoms and particularly 2 to 6 carbon atoms, such as ethanol, isopropanol, propanol, butanol; polyethylene glycols having 6 to 80 ethylene oxide units and polyols such as propylene glycol, isoprene glycol, butylene glycol, glycerin and sorbitol.

The compositions according to the invention may be in any galenic forms conventionally used for topical application and particularly in the form of aqueous, hydroalcoholic solutions, oil-in-water (O/W) or water-in-oil (W/O) or multiple (triple: W/O/W or O/W/O) emulsions, aqueous gels, or oily phase dispersions in an aqueous phase using spherules, wherein said spherules may be polymeric nanoparticles such as nanospheres and nanocapsules or ionic and/or non-ionic type lipid vesicles (liposomes, niosomes, oleosomes). These compositions are prepared using routine methods.

Furthermore, the compositions used according to the invention may be more or less fluid and have the appearance of a white or colored cream, an ointment, milk, lotion, serum, paste, mousse or shampoo.

The composition used according to the invention may comprise adjuvants routinely used in the field of cosmetics, and particularly chosen from water; oils; waxes, pigments, fillers, colorants, surfactants, emulsifiers; cosmetic actives, UV filters, polymers, thickening agents, film-forming polymers, preservatives, perfumes, antibacterial agents, odor absorbers, antioxidants.

The quantities of these various adjuvants are those conventionally used in the field in question, and for example 0.01 to 20% by weight relative to the total weight of the composition.

The invention covers the cosmetic use of one or a plurality of compounds according to the invention, in any of the combinations thereof, preferably in a cosmetic composition containing a physiological acceptable medium, as anti-dandruff agents or for preventing and/or treating scalp dandruff.

It has been observed that, by employing the compounds of formula (I), it is possible to remove and/or reduce the number of yeasts of the *Malassezia* genus, the amount of dandruff.

The invention further covers a cosmetic treatment method for eliminating and/or reducing dandruff, characterized in that it comprises the application, on the scalp, of at least one compound according to the invention or of a cosmetic composition containing said at least one compound.

The examples hereinafter illustrate the invention without limiting the scope thereof, however.

EXAMPLES

A—Examples of Synthesis of Compounds According to the Invention

General Procedure:

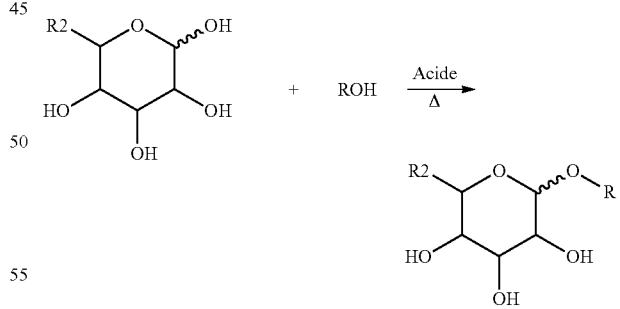

The alcohol (3 eq) is previously heated to a temperature between 40° C. and 90° C. and the sugar (1 eq) and an acidic catalyst, such as for example a sulfonic acid (for example PTSA (paratoluene sulfonic acid), methanesulfonic acid, etc.), hydrochloric acid, sulfuric acid, montmorillonite, acidic resin such as DOWEX, carboxylic acid (citric acid, lactic acid, etc.), (in quantities for example of 0.01 to 0.2 eq) are added. When the reaction is complete (from 1 hour to 48 hours), the reaction medium is cooled, washed and purified by means of silica gel chromatography and/or crystallization.

Example A-1:—hexadecyl 6-deoxy-L-mannopyranoside (rhamnose sugar)

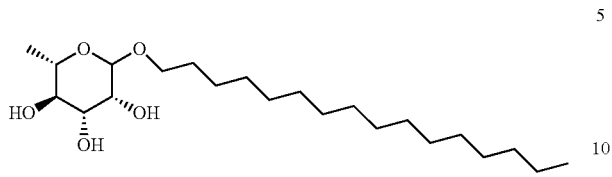

Synthesis described in *International Journal of Cosmetic Science* 2001, 23, 363-368.

Example A-2:—hexadecyl D-xylopyranoside (xylose sugar)

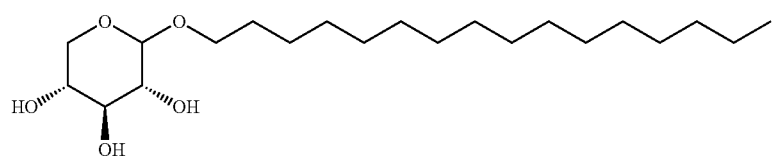 [SMILES: CCCCCCCCCCCCCCCCOC1OC[C@@H](O)[C@H](O)[C@H]1O]

Hexadecanol: 10 g, 41.25 mmol 2.4 eq,
D-xylose: 2.5 g, 16.65 mmol 1 eq
PTSA 250 mg, 1.66 mmol, 0.1 eq.
Reaction time: 18 hours at 80° C.

Xylose and PTSA are added in portions of 1 g+1 g+0.5 g for xylose and 0.1 g+0.1 g+0.05 g for PTSA every 2 hours. The raw product obtained is purified by means of silica gel chromatography. 1.8 g of white powder obtained (Yield=35%).

1H-NMR (400 MHz, DMSO): δ 0.9 (t, 3H), δ 1.3 (m, 27H), δ 1.5 (m, 2H), δ 2.9-3.7 (m, 10H)

Mass spectrometry (ESI+/−MeOH/H$_2$O): [M+Na]$^+$ 397

Micro analyses: 66.9% C, 11.4% H, 20.2% O

Example A-3:—hexadecyl 6-deoxy-L-galactopyranoside (fucose sugar)

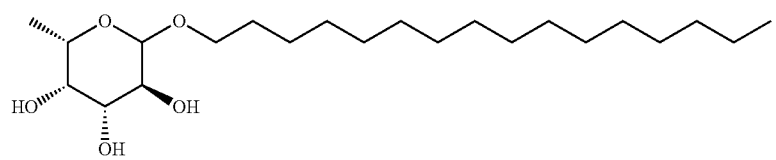

Synthesis described in FR2614024

Example A-4:—octadecyl 6-deoxy-L-mannopyranoside (rhamnose sugar)

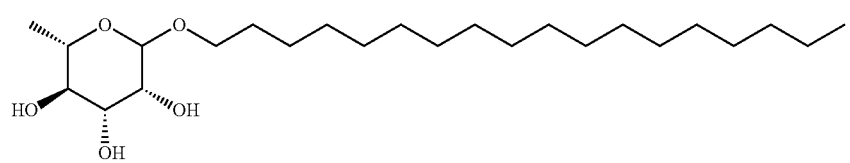 [SMILES: CCCCCCCCCCCCCCCCCCOC1O[C@@H](C)[C@H](O)[C@@H](O)[C@H]1O]

1-octadecanol: 445 mg, 1.6 mmol, 1 eq
L-rhamnose monohydrate: 300 mg, 1.6 mmol, 1 eq
TMSCl (chloro trimethylsilane): 1.04 mL, 8.2 mmol, 5 eq.
Reaction time: 5 min.

After 5 min in a microwave at 60° C. under a pressure of 6 bar, formation of a green precipitate after cooling. The precipitate is dissolved in dichloromethane, the insoluble is filtered and the whole concentrated to remove the residual TMSCl. The raw product is purified on silica gel
41 mg of white powder obtained, yield 6%
Mass spectrometry: M=384.38 [M+Na]+, [M−H]−

Example A-5:—decyl 6-deoxy-L-galactopyranoside (fucose sugar)

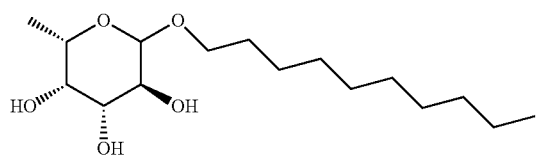 [SMILES: CCCCCCCCCCOC1O[C@@H](C)[C@@H](O)[C@@H](O)[C@@H]1O]

decanol: 35 mL, 0.18 mol,
L-fucose: 10 g, 60.9 mmol, 1 eq
PTSA 1.75 g, 6.09 mmol, 0.1 eq.
Reaction time: 6 hours at 80° C.
5.2 g of fine white powder obtained, yield 29%.
Mass spectrometry: M=304.42 [M+Na]+ et [2M+Na]+ in positive mode and [M−H] in negative mode Example A-6:—decyl 6-deoxy-L-mannopyranoside (rhamnose sugar)

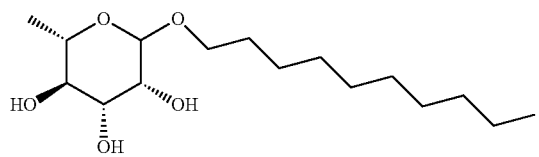 [SMILES: CCCCCCCCCCOC1O[C@@H](C)[C@H](O)[C@@H](O)[C@H]1O]

decanol: 32 mL, 0.16 mol,
L-rhamnose, monohydrate: 10 g, 55 mmol,
PTSA 1.58 g, 5.5 mmol,
Reaction time: 4 hrs 30 at 80° C.
10.52 g obtained in white paste form, yield 65%.
Mass spectrometry: M=304.42 [M−H]−, [M+Na]+

Example A-7:—dodecyl 6-deoxy-L-mannopyranoside (rhamnose sugar)

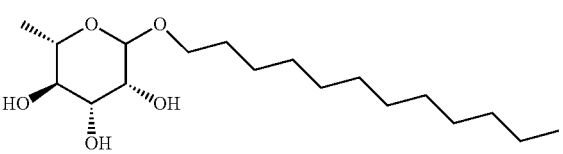 [SMILES: CCCCCCCCCCCCOC1O[C@@H](C)[C@H](O)[C@@H](O)[C@H]1O]

dodecanol: 1.53 g, 8.24 mmol, 5 eq
L-rhamnose monohydrate: 300 mg, 1.6 mmol, 1 eq
TMSCl: 1.04 mL, 8.2 mmol, 5 eq.
Reaction time: 2 hours at 80° C.
310 mg of white powder obtained, yield 56%
Mass spectrometry: M=332.48 [M−H]−, [M+Na]+

Example A-8:—decyl D-xylopyranoside (xylose sugar)

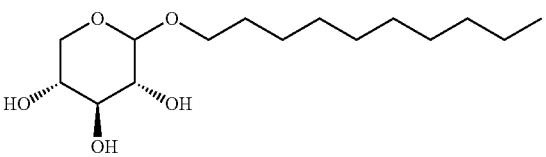 [SMILES: CCCCCCCCCCOC1OC[C@@H](O)[C@H](O)[C@H]1O]

decanol: 32 mL, 0.16 mol 2.5 eq,
D-xylose: 10 g, 66.6 mmol 1 eq,
PTSA 1 g, 6 mmol, 0.1 eq,
Reaction time: 4 hrs 30 at 80° C.
White powder obtained: 1.84 g, yield 10%
Mass spectrometry: M=290.4 [M−H]−, [M+Na]+

Example A-9:—docosyl 6-deoxy-L-mannopyranoside (rhamnose sugar)

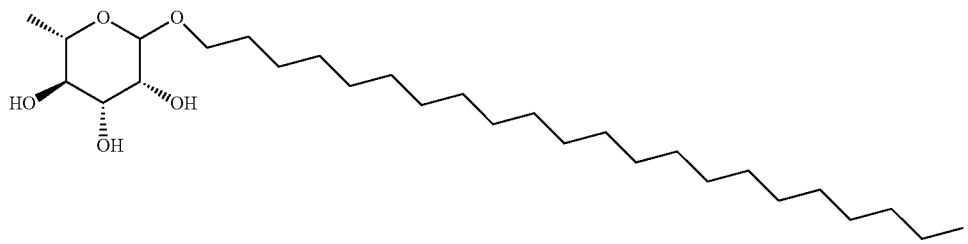 [SMILES: CCCCCCCCCCCCCCCCCCCCCCOC1O[C@@H](C)[C@H](O)[C@@H](O)[C@H]1O]

Docosanol: 54 g, 164 mmol 2 eq,
L-rhamnose: 15 g, 82 mmol 1 eq
PTSA 1.42 g, 8.23 mmol, 0.1 eq.
Reaction time: 6 hours at 80° C.
14.2 g of white powder obtained, yield 36%
Mass spectrometry: M=472, [M+Na]+

Example A-10:—(3S)-3,7-dimethyloct-6-en-1-yl D-xylopyranoside (xylose sugar)

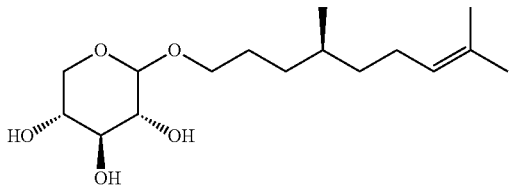 [SMILES: CC(C)=CCC[C@H](C)CCCOC1OC[C@@H](O)[C@H](O)[C@H]1O]

D-xylose: 1 g, 6.7 mmol, 1 eq.
Citronellol: 3.65 mL, 3 eq.
PTSA: 127 mg, 0.67 mmol, 0.1 eq.
Reaction time: 5 hours At the end of the reaction, water and ethyl acetate are added to the reaction medium and the product is extracted, before being purified by means of silica gel chromatography.
400 mg of a yellow oil obtained, yield 20%.

Mass spectrometry: detection of expected product in quasi-molecular ion form [M+H]+ (m/z=289), et [M+Na]+ (m/z=311)

Example A-11:—9-hydroxynonyl 6-deoxy-L-mannopyranoside (rhamnose sugar)

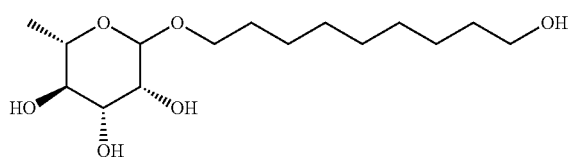 [SMILES: C[C@@H]1OC(OCCCCCCCCCO)[C@H](O)[C@H](O)[C@H]1O]

A mixture containing 1,9-nonane-diol (500 mg), L-rhamnose (1.14 g, 2 equiv.) and 800 mg of Dowex 5WX2 resin in 5 mL of dioxane is heated at 75° C. for 24 hrs. After this time, the resin is filtered, the solvent is evaporated and the residue is purified by means of silica gel column chromatography (CH$_2$Cl$_2$/MeOH: 95/5). The product is obtained in beige paste form (950 mg, yield 17%).

Example A-12:—9-hydroxynonyl-D-mannopyranoside (mannose sugar)

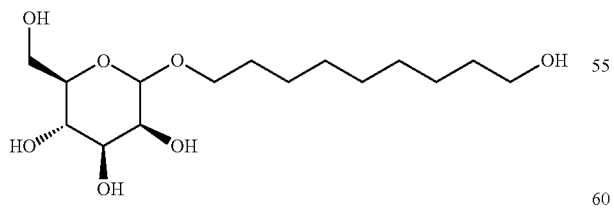

A mixture of D-mannose (2.0 g, 11 mmol, 1 eq.) and 1,9-nonane-diol (5.34 g, 33 mmol, 3 eq.), in the presence of PTSA (210 mg, 1.1 mmol, 0.1 eq.) is heated at 80° C. for 9 hours. The PTSA is subsequently removed using an ion exchange resin and water and ethyl acetate are added to extract the product.

After concentrating the organic phase, recrystallization in acetone makes it possible to obtain an analytically pure sample in white powder form (71 mg).

Example A-13:—2-hydroxydecyl D-xylopyranoside (xylose sugar)

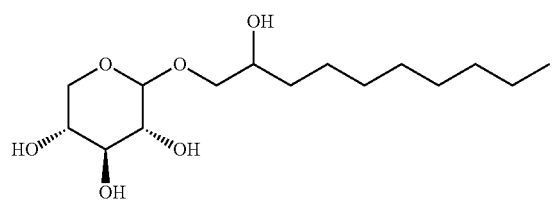 [SMILES: CCCCCCCCC(O)COC1OC[C@@H](O)[C@H](O)[C@H]1O]

A mixture of D-xylose (15 g, 99.9 mmol, 1 eq.) and decane-1,2-diol (52.15 g, 299.74 mmol, 3 eq.), in the presence of PTSA (1.72 g, 9.91 mmol, 0.1 eq.) is heated at 80° C. for 6 hours. The PTSA is subsequently removed using an ion exchange resin and water and ethyl acetate are added to extract the product.

After concentrating the organic phase, recrystallization in acetone makes it possible to obtain an analytically pure sample in white powder form (10.97 g, yield 36%).

B. Examples of Synthesis of Compounds According to Formula (III)

General Procedure:

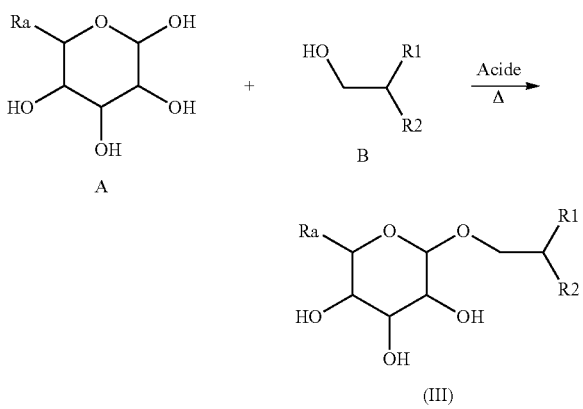

Where Ra=H, CH2OH, Me

The alcohol B (3 eq) is previously heated to a temperature between 40° C. and 90° C. and the sugar A (1 eq) and an acidic catalyst, such as for example a sulfonic acid (for example PTSA, methanesulfonic acid, etc.), hydrochloric acid, sulfuric acid, montmorillonite, acidic resin such as DOWEX, carboxylic acids (citric acid, lactic acid, etc.), (in quantities for example of 0.01 to 0.2 eq) are added. When the reaction is complete (from 1 hour to 48 hours), the reaction medium is cooled, washed and purified by means of silica gel chromatography and/or crystallization.

Example B-1: 2-hexyldecyl 6-deoxy-L-mannopyranoside (rhamnose sugar)

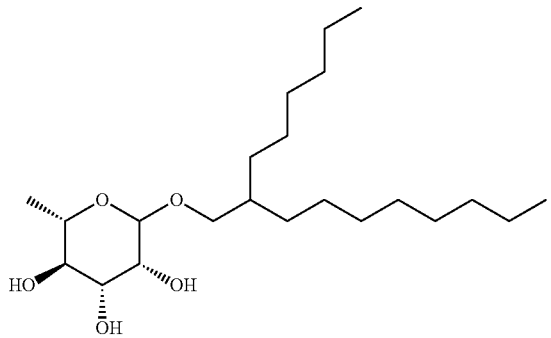 [SMILES: CCCCCCCCC(CCCCCC)COC1O[C@@H](C)[C@H](O)[C@@H](O)[C@H]1O]

A=L-rhamnose-monohydrate: 15 g, 82.3 mmol, 1 eq
B=2-hexyl-1-decanol: 66.46 g, 274.13 mmol, 3.3 eq
Acidic catalyst=PTSA: 1.47 g, 9.13 mmol, 0.11 eq,
Reaction time: 17 hours at 80° C.

At the end of the reaction, ethyl acetate and a saturated NaHCO$_3$ solution are added to the reaction medium and the product is extracted, before being purified by means of silica gel chromatography.

15.44 g of a colorless gel obtained, yield 48%.

Mass spectrometry: detection of expected product in quasi-molecular ion form [M+NH4+]+ (m/z=406)

Example B-2: 2-octyldodecyl 6-deoxy-L-mannopyranoside (rhamnose sugar)

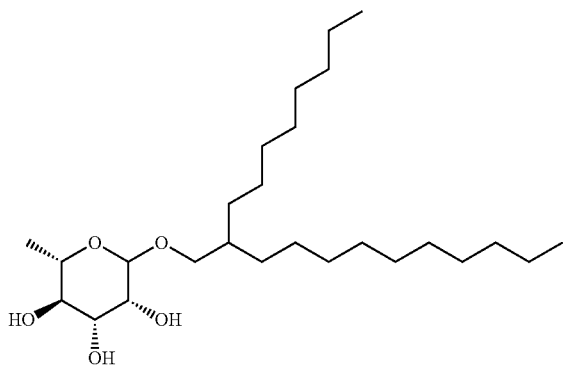 [SMILES: CCCCCCCCCCC(CCCCCCCC)COC1O[C@@H](C)[C@H](O)[C@@H](O)[C@H]1O]

A=L-rhamnose-monohydrate: 15 g, 82.3 mmol, 1 eq
B=2-octyl-1-dodecanol: 49.2 g, 164.68 mmol, 2 eq
Acidic catalyst=PTSA: 1.42 g, 8.23 mmol, 0.1 eq,
Reaction time: 6 hours.

At the end of the reaction, purification by means of silica gel chromatography.

3.7 g of a colorless oil obtained, yield 10%.

Mass spectrometry: detection of expected product in quasi-molecular ion form [M−H]⁻ (m/z=443) and [M+Na]⁺ (m/z=467)

Example B-3: 2-decyltetradecyl 6-deoxy-L-mannopyranoside (rhamnose sugar)

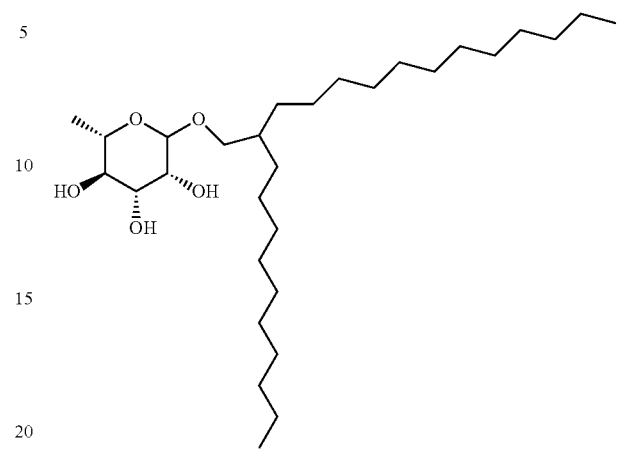

A=L-rhamnose-monohydrate: 15 g, 82.3 mmol, 1 eq
B=2-decyl-1-tetradecanol: 58.41 g, 164.7 mmol, 2 eq
Acidic catalyst=PTSA: 1.42 g, 8.23 mmol, 0.1 eq,
Reaction time: 6 hours at 80° C.

At the end of the reaction, purification by means of silica gel chromatography.

2.6 g of a colorless oil obtained, yield 6%.

Mass spectrometry: detection of expected product in quasi-molecular ion form [M−H]⁻ (m/z=449) and [M+Na+H]⁺ (m/z=524)

In the examples:
TMSCL denotes Chlorotrimethylsilane;
PTSA denotes trisodium 8-aminopyrene-1,3,6-trisulfonate.

C—Cosmetic Compositions According to the Invention

Example C-1: Anti-Dandruff Shampoo

An anti-dandruff shampoo comprising the following ingredients is prepared:

| | |
|---|---|
| Sodium lauryl ether sulfate (2.2 OE) in aqueous solution (COGNIS TEXAPON AOS 225 UP) | 17 g AS |
| Cocoyl betaine in aqueous solution (COGNIS DEHYTON AB 30) | 2.5 g AS |
| Coconut oil acid monoisopropanolamide (GOLDSCHMIDT REWOMID V 3203) | 2.0 g |
| hexadecyl 6-deoxy-L-mannopyranoside | 0.3 g AS |
| Preservatives | 1.1 g |
| Perfume | 0.5 |
| Water | QS 100 g |

Applying the shampoo on the hair and scalp helps reduce the appearance of dandruff.

Example C-2: Anti-Dandruff Lotion

An anti-dandruff lotion comprising the following ingredients is prepared:

| | |
|---|---|
| 2-hexyldecyl 6-deoxy-L-mannopyranoside (example B-1) | 0.3 g AS |
| Preservatives | qs |
| Water | qs 100 g |

Applying the lotion on the hair and scalp helps reduce the appearance of dandruff.

Example D—Assay of Antidandruff Activity

A solution containing 2% by weight of test compound is prepared in "modified Leeming and Notman liquid (MLNA)" in the following way:

0.2 g of test compound is weighed out into quantity sufficient (qs) for 10 mL of modified Leeming and Notman liquid; solubilization is carried out by heating and the use of ultrasound.

The solutions of test product are twice as concentrated as the final test concentration, in order to take into account the dilution when they are brought into contact with the *Malassezia* suspension. By using a solution at 2%, the final concentration evaluated in the test is at 1% after the dilution.

The *Malassezia* strains are brought into contact according to table 2 below:

TABLE 2

|  | Growth control | Test composition |
|---|---|---|
| Strain | 0.5 mL | 0.5 mL |
| Test solution | — | 0.5 mL |
| MLNA medium | 0.5 mL | — |

The mixture is stirred and deposited at the surface of the MLNA agar. It is spread, with a sterile scraper, over the entire surface before recovering the excess. It is left to incubate for at least 5 days at 30° C.

The antifungal effect of the compound is evaluated via the absence of growth of the *Malassezia* strain tested. This inhibition is evaluated relative to the growth control. The inhibitions are scored from 0 to 3 via assessment of the density of the culture at the surface of the agar, in comparison with the growth control, in the following way:

TABLE 3

| Score | Inhibition | Interpretation |
|---|---|---|
| 3 | 100% | No growth |
| 2 | 75% | Growth < in the control dish |
| 1 | 25% | Growth < in the control dish |
| 0 | 0% | Growth comparable to the control dish |

The invention claimed is:

1. A cosmetic treatment method for eliminating and/or reducing dandruff, which comprises applying on the scalp at least one compound according to the following formula (I), as an anti-dandruff agent or for preventing and/or treating scalp dandruff:

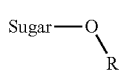
(I)

where "sugar" denotes a monosaccharide residue chosen from rhamnose, xylose, fucose, mannose, lyxose, and arabinose;
where R, substituting the anomeric oxygen in the sugar (represented by "O" in formula (I)), denotes a radical comprising 6 to 38 carbon atoms chosen from:
a linear or branched, saturated alkyl radical;
a linear or branched, alkenyl radical;
said linear or branched saturated alkyl radical being optionally substituted by at least one OH and/or NH$_2$ function;
if "sugar" denotes a mannose residue, R denotes a C6-C38 alkyl radical; substituted by at least one OH function or a NH$_2$ function;
if "sugar" denotes a arabinose residue, R denotes a C6-C38 linear alkyl radical substituted by an OH function or a C9-C38 linear alkyl radical substituted by a NH$_2$ function;
and the salts and solvates and/or optical isomers thereof, alone or in a mixture.

2. The cosmetic treatment method Use according to claim 1, wherein, in compound (I), the sugar is: L-rhamnose, D-xylose, L-fucose, D-mannose, D-lyxose, or arabinose.

3. The cosmetic treatment method according to claim 1, wherein the compound according to formula (I) comprises a radical R comprising 8 to 30 carbon atoms, provided that if "sugar" denotes an arabinose residue and R1 denotes a linear alkyl radical substituted by a NH$_2$ function, said linear alkyl radical comprise at least 9 carbon atoms.

4. The cosmetic treatment method according to claim 1, wherein the compound according to formula (I) is represented by the following formula (II):

(II)

and the salts and solvates, and/or optical isomers thereof, alone or in a mixture,
where R1, substituting anomeric oxygen, denotes:
a linear or branched, saturated C8-C22 alkyl radical;
a linear or branched, C8-C22 alkenyl radical;
a linear C8-C22 alkyl radical, substituted by an OH function or a NH$_2$ function;
if "sugar" denotes a D-mannose residue, R1 denotes a linear C8-C22 alkyl radical, substituted by an OH or NH$_2$ function
if "sugar" denotes an arabinose residue, R1 denotes a linear C8-C22 alkyl radical substituted by an OH or a linear C9-C22 alkyl radical substituted by a NH$_2$ function.

5. The cosmetic treatment method according to claim 4, wherein, in the compound according to formula (II), R1 denotes a C8-C20 saturated linear alkyl radical provided that if "sugar" denotes an arabinose residue and R1 denotes a linear alkyl radical substituted by a NH$_2$ function, said linear alkyl radical comprise at least 9 carbon atoms.

6. The cosmetic treatment method according to claim 4, wherein the compound according to formula (II) is chosen from:
hexadecyl 6-deoxy-L-mannopyranoside
hexadecyl D-xylopyranoside
hexadecyl 6-deoxy-L-galactopyranoside
octadecyl 6-deoxy-L-mannopyranoside
decyl 6-deoxy-L-galactopyranoside
decyl 6-deoxy-L-mannopyranoside
dodecyl 6-deoxy-L-mannopyranoside
decyl D-xylopyranoside
docosyl 6-deoxy-L-mannopyranoside
(3S)-3,7-dimethyloct-6-en-1-yl D-xylopyranoside
9-hydroxynonyl 6-deoxy-L-mannopyranoside
9-hydroxynonyl-D-mannopyranoside
2-hydroxydecyl D-xylopyranoside
octyl 6-deoxy-L-mannopyranoside eicosyl 6-deoxy-L-mannopyranoside
dodecyl 6-deoxy-L-mannopyranoside
tetradecyl 6-deoxy-L-mannopyranoside
decyl D-lyxopyranoside,
and mixtures thereof.

7. The cosmetic treatment method according to claim 1, wherein the compounds according to formula (I) are represented by the following formula (III):

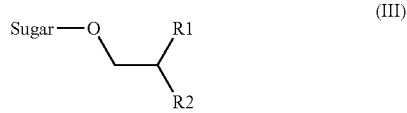

and the salts and solvates and/or optical isomers thereof, alone or in a mixture,
where "sugar" denotes a monosaccharide residue chosen from rhamnose, xylose, fucose, mannose, lyxose, and arabinose;
R1 denotes a linear C2-C18 alkyl radical;
R2 denotes a linear C2-C18 alkyl radical
if "sugar" denotes an arabinose residue, R1 denotes a linear C8-C22 alkyl radical substituted by an OH or a linear C9-C22 alkyl radical substituted by a NH$_2$ function.

8. The cosmetic treatment method according to claim 7, wherein:
the compound according to formula (III) is chosen from:
2-octyltetradecyl 6-deoxy-L-mannopyranoside
2-octyldecyl 6-deoxy-L-mannopyranoside
2-hexyldecyl 6-deoxy-L-mannopyranoside
2-octyldodecyl 6-deoxy-L-mannopyranoside
2-decyltetradecyl 6-deoxy-L-mannopyranoside
2-octyltetradecyl D-lyxopyranoside
2-octyldodecyl D-lyxopyranoside
2-decyltetradecyl D-lyxopyranoside
2-hexyldecyl 6-deoxy-L-galactopyranoside
2-octyldodecyl 6-deoxy-L-galactopyranoside
2-decyltetradecyl 6-deoxy-L-galactopyranoside
2-octyltetradecyl D-mannopyranoside
2-octyldodecyl D-mannopyranoside
2-decyltetradecyl D-mannopyranoside
and mixtures thereof.

9. The cosmetic treatment method according to claim 1, wherein one or a plurality of said at least one compound are present in a cosmetic composition containing a physiologically acceptable medium.

10. A compound according to the following formula (I'):

and the salts and solvates and/or optical isomers thereof, alone or in a mixture, where:
the sugar is a rhamnose and R is a C6-C38 linear alkyl radical substituted by an OH function;
the sugar is a rhamnose and R is a C8-C38 linear alkyl radical substituted by a NH$_2$ function;
the sugar is a mannose and R is a C8-C38 linear alkyl radical substituted by an OH function;
the sugar is a mannose and R is a C14-C38 saturated linear alkyl radical substituted by a NH$_2$ function;
the sugar is a xylose and R is a C6-C38 linear alkyl radical substituted by an OH function;
the sugar is a xylose and R is a C9-C38 linear alkyl radical substituted by a NH$_2$ function;
the sugar is a lyxose and R is a C6-C38 linear alkyl radical substituted by an OH function;
the sugar is a lyxose and R is a C8-C38 linear alkyl radical substituted by a NH$_2$ function;
the sugar is a fucose and R is a C6-C38 linear alkyl radical substituted by an OH function;
the sugar is a fucose and R is a C9-C38 linear alkyl radical substituted by a NH$_2$ function;
the sugar is an arabinose and R is a C6-C38 linear alkyl radical substituted by an OH function;
the sugar is an arabinose and R is a C9-C38 linear alkyl radical substituted by a NH$_2$ function;
or
the sugar denotes a monosaccharide residue chosen from rhamnose, fucose, lyxose, and arabinose, and R represents:

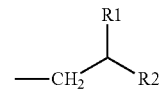

where
R1 denotes a linear C2-C18 alkyl radical; and
R2 denotes a linear C2-C18 alkyl radical,
if "sugar" denotes an arabinose residue, R1 denotes, a linear C8-C22 alkyl radical substituted by an OH or a linear C9-C22 alkyl radical substituted by a NH$_2$ function.

11. The compound according to claim 10, being chosen from the following compounds
9-hydroxynonyl 6-deoxy-L-mannopyranoside;
9-hydroxynonyl-D-mannopyranoside;
2-hydroxydecyl D-xylopyranoside;
2-octyltetradecyl 6-deoxy-L-mannopyranoside;
2-octyldecyl 6-deoxy-L-mannopyranoside;
2-hexyldecyl 6-deoxy-L-mannopyranoside;
2-octyldodecyl 6-deoxy-L-mannopyranoside;
2-decyltetradecyl 6-deoxy-L-mannopyranoside;
2-octyltetradecyl D-lyxopyranoside;
2-octyldodecyl D-lyxopyranoside;
2-decyltetradecyl D-lyxopyranoside;
2-hexyldecyl 6-deoxy-L-galactopyranoside;
2-octyldodecyl 6-deoxy-L-galactopyranoside;
2-decyltetradecyl 6-deoxy-L-galactopyranoside;
2-octyltetradecyl D-mannopyranoside;
2-octyldodecyl D-mannopyranoside;
2-decyltetradecyl D-mannopyranoside.

12. A cosmetic composition which comprises at least one compound as defined according to claim 10 and a physiologically acceptable medium.

13. A cosmetic treatment method for eliminating and/or reducing dandruff, which comprises the application, on the scalp, of a cosmetic composition containing said at least one compound according to claim 2.

14. The cosmetic treatment method according to claim 2, wherein the compound according to formula (I) comprises a radical R comprising 8 to 30 carbon atoms provided that if "sugar" denotes an arabinose residue and R1 denotes a linear alkyl radical substituted by a NH$_2$ function, said linear alkyl radical comprise at least 9 carbon atoms.

15. The cosmetic treatment method according to claim 1, wherein, in compound (I), the sugar is: chosen from:
- 6-deoxy-L-mannopyranoside;
- 6-deoxy-L-galactopyranoside;
- D-xylopyranoside;
- D-lyxopyranoside; and
- L-arabinopyranoside.

16. The cosmetic treatment method according to claim 2, wherein the compound according to formula (I) is represented by the following formula (II):

(II)

and the salts and solvates, and/or optical isomers thereof, alone or in a mixture,
where R1, substituting anomeric oxygen, denotes:
- a linear or branched, saturated C8-C22 alkyl radical;
- a linear or branched, C8-C22 alkenyl radical;
- a linear C8-C22 alkyl radical, substituted by an OH function or $NH_2$ function;
- if "sugar" denotes a D-mannose residue, R1 denotes a linear C8-C22 alkyl radical, substituted by an OH or $NH_2$ function
- if "sugar" denotes an arabinose residue, R1 denotes a linear C8-C22 alkyl radical substituted by an OH or a linear C9-C22 alkyl radical substituted by a $NH_2$ function.

17. The cosmetic treatment method according to claim 2, wherein, in the compound according to formula (I), R denotes a C8-C20 saturated linear alkyl radical, provided that if "sugar" denotes an arabinose residue and R1 denotes a linear alkyl radical substituted by a $NH_2$ function, said linear alkyl radical comprise at least 9 carbon atoms.

18. The cosmetic treatment method according to claim 3, wherein, in the compound according to formula (I), R denotes a C8-C20 saturated linear alkyl radical, provided that if "sugar" denotes an arabinose residue and R1 denotes a linear alkyl radical substituted by a $NH_2$ function, said linear alkyl radical comprise at least 9 carbon atoms.

19. The cosmetic treatment method according to claim 4, wherein, in the compound according to formula (II), R1 denotes a C8-C20 saturated linear alkyl radical, provided that if "sugar" denotes an arabinose residue and R1 denotes a linear alkyl radical substituted by a $NH_2$ function, said linear alkyl radical comprise at least 9 carbon atoms.

20. The cosmetic treatment method according to claim 2, wherein the compound according to formula (I) is chosen from:
- hexadecyl 6-deoxy-L-mannopyranoside
- hexadecyl D-xylopyranoside
- hexadecyl 6-deoxy-L-galactopyranoside
- octadecyl 6-deoxy-L-mannopyranoside
- decyl 6-deoxy-L-galactopyranoside
- decyl 6-deoxy-L-mannopyranoside
- dodecyl 6-deoxy-L-mannopyranoside
- decyl D-xylopyranoside
- docosyl 6-deoxy-L-mannopyranoside
- (3S)-3,7-dimethyl oct-6-en-1-yl D-xylopyranoside
- 9-hydroxynonyl 6-deoxy-L-mannopyranoside
- 9-hydroxynonyl-D-mannopyranoside
- 2-hydroxydecyl D-xylopyranoside
- octyl 6-deoxy-L-mannopyranoside
- eicosyl 6-deoxy-L-mannopyranoside
- dodecyl 6-deoxy-L-mannopyranoside
- tetradecyl 6-deoxy-L-mannopyranoside
- decyl D-lyxopyranoside, and mixtures thereof.

* * * * *